(12) United States Patent
Bales

(10) Patent No.: US 7,883,651 B1
(45) Date of Patent: Feb. 8, 2011

(54) LIGNOELLULOSIC, BORATE FILLED, THERMOPLASTIC COMPOSITES

(75) Inventor: Stephen G. Bales, Sewell, NJ (US)

(73) Assignee: Lords Additives LLC, Sewell, NJ (US)

(*) Notice: Subject to any disclaimer, the term of this patent is extended or adjusted under 35 U.S.C. 154(b) by 822 days.

(21) Appl. No.: 10/681,497

(22) Filed: Oct. 8, 2003

Related U.S. Application Data

(60) Provisional application No. 60/427,113, filed on Nov. 18, 2002.

(51) Int. Cl.
*B29C 43/00* (2006.01)

(52) U.S. Cl. ...................................... 264/122; 264/241

(58) Field of Classification Search ................. 264/122, 264/241
See application file for complete search history.

(56) References Cited

U.S. PATENT DOCUMENTS

| | | | |
|---|---|---|---|
| 3,865,760 A | | 2/1975 | Pitts et al. |
| 3,926,883 A | * | 12/1975 | Touval ........................ 524/405 |
| 4,076,580 A | | 2/1978 | Panusch et al. |
| 4,104,207 A | * | 8/1978 | Pelikan et al. ............. 521/84.1 |
| 4,879,083 A | | 11/1989 | Knudson et al. |
| 4,891,399 A | * | 1/1990 | Ohkawa et al. ............. 523/200 |
| 4,935,457 A | | 6/1990 | Metzner et al. |
| 5,130,352 A | * | 7/1992 | Chow ........................... 524/13 |
| 5,221,781 A | * | 6/1993 | Aida et al. ................... 524/433 |
| 5,246,652 A | | 9/1993 | Hsu et al. |
| 5,435,954 A | * | 7/1995 | Wold ........................... 264/115 |
| 5,482,989 A | * | 1/1996 | Koskiniemi ................. 524/404 |
| 5,514,478 A | * | 5/1996 | Nadkarni ..................... 428/469 |
| 5,525,757 A | | 6/1996 | O'Brien |
| 5,549,739 A | | 8/1996 | Inoue et al. |
| 5,763,338 A | | 6/1998 | Sean |
| 5,972,266 A | | 10/1999 | Fookes et al. |
| 6,096,816 A | | 8/2000 | Kuckro |
| 6,368,529 B1 | | 4/2002 | Manning et al. |
| 6,416,789 B1 | | 7/2002 | Marks et al. |
| 6,723,352 B2 | | 4/2004 | Bosserman |
| 6,881,247 B2 | | 4/2005 | Batdorf |
| 7,056,919 B2 | | 6/2006 | Ross et al. |
| 2002/0182431 A1 | | 12/2002 | Hatton et al. |
| 2003/0071389 A1 | * | 4/2003 | Manning et al. ............ 264/122 |

FOREIGN PATENT DOCUMENTS

WO WO/2006/014428 A1 2/2006

OTHER PUBLICATIONS

Steven Verhey, Peter Laks, Dana Richter, "Laboratory Decay Resistance of Woodfiber/Thermoplastic Composites", Forest Products Journal, vol. 51, Sep. 2001, p. 44-50.
Mark Mankowski and Jeffrey J. Morrell, Patterns of Fungal Attack in Wood-Plastic Composites Following Exposure in a Soil Block Test, Wood and Fiber Science, Jul. 2000, p. 340-345.
David Pendleton, et al, "Durability of an Extended HDPE/Wood Composite", Forest Products Journal, vol. 52, Jun. 2002, p. 21-27.
Peter Laks and Mark Manning, "Preservation of Wood Composites with Zinc Borate", Paper for The International Research Group on Wood Preservation, Jun. 1995.
Fred Moore and William Kennelly, Effect of Co-Additives on the Flame/Smoke Supression Properties of Zinc Borate, Journal of Vinyl Technology, vol. 13, Sep. 1991, p. 169-173.
David R. Lide, Editor CRC Handbook of Chemistry and Physics, Ed. 86, 2005, p. 4-96.
P.I. Morris, "Understanding Biodeterioration of Wood in Structures", Forintek Canada Corp Publication, 1997, p. 1-23.
Craig Clemons "Wood-Plastic Composites in the United States—The Interfacing of Two Industries", Forest Products Journal, Jun. 2002, p. 10-18.
Path, "Recycled Wood/Plastic Composite Lumber" Sep. 2005, 3 page report.
PI Morris, Paul Cooper, "Recycled Plastic/Wood Composite Lumber Attacked by Fungi", Forest Products Journal, Jan. 1998, p. 86-88.
Zohar Karem, Kenneth Hammel, Wuli Bao, "Extracellular Degradation of Polyethers by the Brown Rot Fungus *Gloeophyllum trabeum*", 1997 Biological Sciences Symposium, Oct. 19, 1997.
Efficacy Review, EPA Report, Nov. 26, 1984.
Concordia University Fungai Genomics Projects, report on Trametes versicolor, *Gloephyllum trabeum*, and *Aspergillus niger*.
Superior Court of New Jersey, Jul. 31, 2004.

(Continued)

*Primary Examiner*—Christina Johnson
*Assistant Examiner*—Galen Hauth

(57) ABSTRACT

The incorporation of borates during the manufacture of lignocellulosic based thermoplastic materials containing about 25 to 75 percent by weight of the thermoplastic material will increase their resistance to surface impairment caused by mold as well as increase their resistance to fungal decay. For resistance to surface impairment, the preferred amount is 3 to 5 percent of the boron containing fungicide. When fungal decay resistance is needed the preferred amount is about 0.3 to 2 percent of the boron containing fungicide.

1 Claim, No Drawings

OTHER PUBLICATIONS

Peter Laks, Klay Vehring, Steven Verhey, and Dana Richter, "Effect of Manufacturing Variables on Mold Susceptibility of Wood-Plastic Composites", 8th conf. on Woodfiber-Plastic Composites, May 23, 2005.

Urs Buehlmann, Daniel Saloni, Richard L. Lemaster, "Wood Fiber-Plastic Composites: Machining and Surface Quality", 15th International Wood Machining Seminar, Jul. 30, 2001.

J.E. Winandy, N.M. Stark, C.M. Clemons,'Considerations in Recycling of Wood-Plastic Composites, USDA Forest Service, Apr. 2004.

Peter Dylingowski, "Maintaining the Aesthetic Quality of WPC Decking With Isothiazolone Biocide", 7th Intl conf. on Woodfiber-Plastic Composites Forest Products Society, May 20, 2003.

EPA Label: Borogard Zinc Borate, Technical Data Sheet, 3 pages-reference: p. 2: Wood Composite Materials: Jul. 26, 2003.

Peter Laks, "Effect of Manufacturing Variables on Mold Susceptibility of Wood-Plastic Composites", Paper submitted to the 8th Intl Conference of Woodfiber-Plastic Composites, Forest Products Society, May 23, 2005.

List of Publications: Dr. Peter Laks, Michigan Technical University, MTU Internet Publication, Mar. 2007.

Technical Notes, Engineered Wood Association, Nov. 2000, 2 pages.

Fogel, J & Lloyd J,, "Mold Performance of Some Construction Products With and Without Borates", Forest Products Journal, Feb. 2002 vol. 52, p. 38-43.

Carlton Holmes, "Effect of Fire-Retardant Treatments on Performance Properties of Wood", Ch 6 of Wood Technology Chemical Aspects, American Chemical Society, 1977 (p. 82-89) (Article continues to p. 106).

Verhey. S & Laks, P, "Wood Particle Size Affects the Decay Resistance of Woodfiber/Thermoplastic Composites" Forest Products Journal, vol. 52,, 2002, p. 1-4.

EPA Label: Borogard Zinc Borate, Technical Data Sheet, 3 pages-reference: p. 2: Wood Composite Materials: Jul. 26, 1993. (Typographical error was made on previous IDS #4, incorrectly indicating the Borogard label date as 2003).

Arkansas Business "Class Settlement in AERT Deck Cleaning Lawsuit" Jan. 19, 2009.

* cited by examiner

LIGNOELLULOSIC, BORATE FILLED, THERMOPLASTIC COMPOSITES

CROSS-REFERENCE TO RELATED APPLICATIONS

This is a Provisional of Ser. No. 60/427,113 filed Nov. 18, 2002.

FEDERALLY SPONSORED RESEARCH

None

SEQUENCE LISTING

None

BACKGROUND

This invention relates to lignocellulosic composites, and more particularly, to lignocellulosic, borate filled, thermoplastic composites.

There is a very high demand for wood products. Although wood is a renewable resource, it takes many years for trees to mature. Consequently, the supply of wood suitable for use in construction is decreasing and there is a need to develop alternatives.

Lignoelluosic materials, such as wood, sawdust, rice hulls, and the like have long been added to thermoplastic resins such as polyethylene, polypropylene and polyvinyl chloride (PVC) to achieve a wood-like composite providing reinforcement, reduced coefficient of expansion, and cost reduction. Process methods have been developed to enable blends containing materials having low bulk density (ie. powders) and poor flow characteristics to be fed at commercially acceptable rates. Blends of this type can be extruded through dies of appropriate configuration to produce building product type shapes previously made from wood. When these thermoplastic composites were first introduced, the prevailing theory was that the plastic protected the cellulose from fungal attack. However research by Verhey, Laks, and Richer, described in "Laboratory Decay Resistance of Woodfiber/Thermoplastic Composites", Forest Products Journal, September 2001 revealed that lignocellulosic thermoplastics are susceptible to damage from fungal decay. Degradation due to the fungal attack is a problem that threatens the material's structural integrity. In contrast, surface discoloration and spotting has been reported shortly after the introduction of thermoplastic composites. This visual degradation, caused by mold, is a significant problem since major commercial uses of lignocellulosic thermoplastic composites, including decking and fencing, rely on their aesthetic appeal to compete in the marketplace.

Traditionally, solid wood products are dipped or pressure treated with solutions of fungicides to provide resistance to fungus and mold damage. While this type of treatment is not practicable for a thermoplastic product, it is possible to incorporate a fungicide into the product during its manufacture. This approach provides a constant loading of fungicide throughout the material's thickness, increasing the resistance to leaching of the fungicide from the composite. However it diminishes surface concentration of the fungicide, reducing its effectiveness against surface mold attack. Anhydrous borate and zinc borate have been used successfully to provide fungal decay at relatively low levels, typically less than 1.5 percent, in lignocellulosic compounds formed from small fractions of wood bonded with an adhesive binder of phenol-formaldehyde resin as described in U.S. Pat. No. 4,879,083. Zinc borate has also been described in the literature as providing resistance to fungal decay in lignocellulosic filled thermoplastics. Research on zinc borate's use as an anti-fungal additive in lignocellulosic thermoplastics has focused on the minimum loading required to increase resistance to fungal decay, while neglecting to consider or investigate the effect of those higher loading levels required to provide resistance to visual deterioration caused by surface molds.

Although not used commercially as a fungicide, calcium borate is described in U.S. Pat. No. 6,368,529 and Patent Application No 20020182431 as providing protection against fungal decay and insects in lignocellulosic compounds formed from small fractions of wood bonded with an adhesive binders of phenol-formaldehyde, phenol-resorcinol-formaldehyde, urea-formaldehyde, and diphenylmethanediisocyanate at preferred levels of 1.5% to 15%. All investigation done on the use of calcium borate as a fungicide has focused on its ability to resist fungal decay in lignocellulosic composites such as particleboard, waferboard, oriented strandboard, and medium density fiberboard that use these thermosetting resins.

Currently the lignocellousic thermoplastics industry is faced with two preservation needs: (1) finding an economic method of improving resistance to fungal decay and (2) developing an economic method for improving resistance to the visual damage caused by surface mold.

SUMMARY AND OBJECTIVES OF THE INVENTION

The present invention, which addresses the above needs, is the incorporation of borates to improve the durability of lignocellulosic thermoplastic products. More specifically it relates to the use of boron-containing fungicides as a preservative to economically increase the resistance of lignocellulosic thermoplastic products to structural decay caused by fungus and to increase the resistance to the visual impairment of the product's surface caused by mold.

It is an object of the invention is to provide an economic, environmentally safe method of increasing the resistance of a lignocelloulsic thermoplastic to fungal decay. This is accomplished by the introduction of economic, low toxicity borate materials including calcium borate and boric acid.

It is a further objective of the invention is to provide an economic, environmentally safe method whereby the lignocellousic thermoplastic has an increased resistance to surface discoloration and other visual impairments caused by mold. It was discovered this can only be accomplished by increasing the borate loading above the 2 percent level by weight. The invention utilizes the robust nature of the thermoplastic binders to accommodate these increased loadings without creating strength or dimensional problems and resulted in the unexpected discovery that borate loading levels as low as 3 percent can provide a significantly increased resistance to surface mold.

DETAILED DESCRIPTION

The lignocellulosic thermoplastic composites of this invention are produced by well known procedures that combine molten plastic with lignocellulosic fiber and additional additives such as lubricants, process aids, cross-linking agents, inhibitors, stabilizers, blowing agents, foaming agents and other additives known in the art. Examples of suitable thermoplastics include polyethylene (PE), high density polyethylene (HDPE), polystyrene (PS), and polyvinyl chloride (PVC) with loadings by weight from 25% to 75%. This process is further described in U.S. Pat. No. 5,516,472 (May, 1996). Examples of suitable cellulosic material include wood, ground rice hulls, kenaf, jute, and coconut shells.

The methods for manufacturing cellulosic filled thermoplastic are well known and the specific procedure will be dependent on the cellulosic raw material, the plastic, and the type of cellulosic thermoplastic composite desired. However, in general the raw materials are mixed together in a compounding process and the compounded material is then formed into the desired product. Compounding is the feeding and dispersing of fillers and additives, including the fungicide which is in powder form, into the molten polymer using either batch or continuous mixers. The compounded material then is either immediately pressed into the end product or formed into pellets for future processing.

As used in this invention, the term "boron-containing fungicide" includes calcium borate, zinc borate, and boric acid. The calcium borate which can be used in the method of this invention may be any of the borate compounds containing calcium, boron, and oxygen. This includes calcium borates that may be synthetically produced or naturally occurring borates including colemanite, ulexite, nobelite, hydroboracite, and gowerite.

The exact particle size of the boron-containing fungicide is not critical, but the material must be of a size that can be dispersed uniformly throughout the lignocellulosic thermoplastic composite. Generally a mean particle size as large as 150 microns and as small as 1 micron can be used. For best results the mean particle size should be in the range of 40 microns to 5 microns.

The amount of boron-containing fungicide incorporated into the lignocellulosic thermoplastic composite will depend on the lignocellulosic content, the longevity desired and the anticipated exposure to moisture. In general, when resistance to decay caused by fungus is required, a range of about 0.2 to 5 percent by weight of the fungicide is required. The preferred amount is about 0.3 to 2 percent.

When resistance to visual impairment to the surface caused by mold is required, the amount will be in the range of about 2 to 12 percent. The preferred amount is about 3 to 5 percent.

EXAMPLES

Example 1

Lignocellulosic thermoplastic material was produced using a Brabender Conical Twin Screw Extruder with a counter rotating venting screws and forced through a spring die into test samples 40 cm by 5 cm by 0.2 cm. Prior to extrusion the test samples were blended on a Littleford W-10 mixer as identical mixtures of High Density Polyethylene (HDPE) (>25%), Wood (>40%), Talc (>5%) and Mica (>1%) but with Colemanite loadings of 1, 2, 3, 4, and 5 percent by weight. A sample containing no Colemanite was produced as the control. The Colemanite grade was 47.5% $B_2O_3$, the HDPE was a BP Solvay virgin reactor flake, and the wood was oak.

The five test samples and the control sample were placed in an outdoor exposure for eighteen (18) months. Visual observations and color recordings using with a Macbeth Color-Eye 7000A spectrophotometer were taken at 6, 12, and 18 months (see Table I). When, after 18 months, the six samples were placed next to one another in ascending order by the level of colemanite content a visible improvement was evident as the level of colemanite increased. The control sample had darkened in appearance considerably more that the colemanite containing samples as can be confirmed by the color data shown in Table 1. The samples containing 3, 4, and 5 percent colemanite are all relatively similar in color and obtained the best visual appearance of the six sample set.

As the results show, this calcium borate based material can improve resistance to visual impairment caused by surface mold.

TABLE 1

| Sample | L | a | b | ΔL | Δa | Δb | ΔE |
|---|---|---|---|---|---|---|---|
| Control | | | | | | | |
| Initial | 64.713 | 2.266 | 10.328 | | | | |
| 6 month | 68.443 | 0.172 | 2.879 | 3.730 | −2.095 | −7.431 | 8.574 |
| 12 month | 64.438 | −0.009 | 1.951 | −0.275 | −2.276 | −8.377 | 8.685 |
| 18 month | 63.158 | 0.007 | 1.944 | −1.555 | −2.260 | −8.384 | 8.821 |
| Colemanite 1% | | | | | | | |
| Initial | 64.968 | 2.558 | 10.493 | | | | |
| 6 month | 69.138 | 0.181 | 2.836 | 4.170 | −2.378 | −7.657 | 9.037 |
| 12 month | 65.673 | 0.033 | 2.286 | 0.705 | −2.525 | −8.207 | 8.616 |
| 18 month | 64.609 | 0.033 | 2.406 | −0.359 | −2.525 | −8.087 | 8.480 |
| Colemanite 2% | | | | | | | |
| Initial | 65.675 | 2.382 | 10.059 | | | | |
| 6 month | 69.278 | 0.217 | 2.903 | 3.603 | −2.165 | −7.156 | 8.299 |
| 12 month | 67.195 | −0.031 | 2.154 | 1.519 | −2.413 | −7.905 | 8.404 |
| 18 month | 65.348 | 0.050 | 2.469 | −0.327 | −2.332 | −7.590 | 7.947 |
| Colemanite 3% | | | | | | | |
| Initial | 66.452 | 2.298 | 9.921 | | | | |
| 6 month | 69.884 | 0.171 | 2.923 | 3.392 | −2.127 | −6.998 | 8.062 |
| 12 month | 68.417 | −0.021 | 2.331 | 1.965 | −2.319 | −7.590 | 8.176 |
| 18 month | 66.678 | 0.057 | 2.797 | 0.226 | −2.241 | −7.124 | 7.471 |
| Colemanite 4% | | | | | | | |
| Initial | 65.957 | 2.307 | 9.824 | | | | |
| 6 month | 68.272 | 0.195 | 3.102 | 2.315 | −2.112 | −6.722 | 7.417 |
| 12 month | 68.208 | 0.020 | 2.572 | 2.251 | −2.286 | −7.253 | 7.930 |
| 18 month | 66.048 | 0.115 | 3.075 | 0.091 | −2.192 | −6.749 | 7.097 |
| Colemanite 5% | | | | | | | |
| Initial | 66.106 | 2.353 | 10.087 | | | | |
| 6 month | 69.661 | 0.187 | 3.010 | 3.554 | −2.166 | −7.077 | 8.210 |
| 12 month | 67.495 | 0.000 | 2.514 | 1.388 | −2.352 | −7.572 | 8.050 |
| 18 month | 66.964 | 0.066 | 2.914 | 0.857 | −2.286 | −7.173 | 7.277 |

Lignocellulosic thermoplastic material was produced using a Brabender Conical Twin Screw Extruder with a counter rotating venting screws and forced through a spring die into test samples 40 cm by 5 cm by 0.2 cm. Prior to extrusion two sets of samples were blended on a Littleford W-10 mixer; set 1 contained Wood (70%), High Density Polyethylene (HDPE) (<30%), Talc (>5%) and Mica (>1%) while set 2 was identical but with the addition of a 2 percent Colemanite loading by weight. The Colemanite grade was 47.5% $B_2O_3$; the HDPE was a BP Solvay virgin reactor flake, and the wood was oak.

The samples were sanded and trimmed to 3.2 cm by 2 cm by 0.2 cm. Labeled samples were supported on plastic mesh in the bottom of beakers to allow water circulation completely around the samples, covered with 250 mL of distilled water, and soaked continuously for 14 days at ambient pressure and temperature. The test specimens were then dried at 40° C. to dry for 7 days. Then, the test specimens were placed in a 27° C., 90% humidity environment for 20 days prior to soil block testing.

The soil block test was conducted in accordance with the American Wood-Preservers Association (AWPA) standard procedure E10-91 with the exception that the brown rot samples were placed in jars at the time of inoculation. The white rot fungus *Trametes versicolor* and the brown rot fungus *Gloeophyllum trabeun* were used for the test. Solid wood controls were paper birch and southern yellow pine (SYP) for the white and brown rot tests, respectively as a test of fungal vigor. The following results were obtained:

TABLE 2a

SOIL BLOCK TEST RESULTS
White Rot test (Gloephyllum trabeum)

| Sample Group | Sample # | Weight Loss % | Average % | Std Deviation % |
| --- | --- | --- | --- | --- |
| Untreated Birch Control | B-1 | 67.1 | | |
| | B-2 | 63.9 | | |
| | B-3 | 66.9 | | |
| | B-4 | 66.9 | | |
| | B-5 | 65.1 | 66.0 | 1.4 |
| Sample Set 1 No preservative | 1-1 | 33.1 | | |
| | 1-2 | 39.6 | | |
| | 1-3 | 40.4 | | |
| | 1-4 | 26.0 | | |
| | 1-5 | 37.8 | 35.4 | 6.0 |
| Sample Set 2 2% Colemanite | 2-1 | 5.1 | | |
| | 2-2 | 4.7 | | |
| | 2-3 | 2.2 | | |
| | 2-4 | 4.8 | | |
| | 2-5 | 2.7 | 3.9 | 1.4 |

TABLE 2b

Brown Rot test (Gloephyllum trabeum)

| Sample Group | Sample # | Weight Loss % | Average % | Std Deviation % |
| --- | --- | --- | --- | --- |
| Untreated SYP Control | P-1 | 62.0 | | |
| | P-2 | 48.6 | | |
| | P-3 | 50.7 | | |
| | P-4 | 43.0 | | |
| | P-5 | 40.8 | 49.0 | 8.3 |
| Sample Set 1 No preservative | 1-6 | 38.6 | | |
| | 1-7 | 35.2 | | |
| | 1-8 | 36.5 | | |
| | 1-9 | 38.1 | | |
| | 1-10 | 41.7 | 38.0 | 2.5 |
| Sample Set 2 2% Colemanite | 2-6 | 11.2 | | |
| | 2-7 | 11.8 | | |
| | 2-8 | 3.0 | | |
| | 2-9 | 9.4 | | |
| | 2-10 | 9.6 | 9.0 | 3.5 |

As the above results show, this calcium borate based additive was effective at controlling *Trametes versicolor* and *Gloeophyllum trabeum*. And, as discovered above, at even this relatively low loading the additive would improve resistance to surface discoloration caused by mold.

What is claimed is:

1. In the method for forming a composite product consisting of a polyolefin material which is 25 to 75 percent by weight of the total composite, a lignocellulosic material, talc, mica, and optionally and at least one of the group consisting of a lubricant, a cross-linking agent, a UV stabilizer, an inhibitor, a colorant, and a coupling agent such as to increase their resistance to surface visual impairment caused by mold attack, the improvement which consists of incorporating an amount of a cationic salt of boric acid selected from the group of synthetic calcium borate, colemanite, ulexite, or mixtures thereof in the range of from about 2 to 12 percent by weight of said composite product.

\* \* \* \* \*